(12) United States Patent
Woollam et al.

(10) Patent No.: US 7,030,982 B1
(45) Date of Patent: Apr. 18, 2006

(54) COMBINED USE OF OSCILLATING MEANS AND ELLIPSOMETRY TO DETERMINE UNCORRELATED EFFECTIVE THICKNESS AND OPTICAL CONSTANTS OF ACCUMULATED MATERIAL

(75) Inventors: John A. Woollam, Lincoln, NE (US); James D. Welch, Omaha, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 339 days.

(21) Appl. No.: 10/746,924

(22) Filed: Dec. 25, 2003

Related U.S. Application Data

(60) Provisional application No. 60/437,024, filed on Dec. 31, 2002.

(51) Int. Cl.
*G01J 4/00* (2006.01)

(52) U.S. Cl. .................................. 356/369; 356/630
(58) Field of Classification Search ............... None
See application file for complete search history.

(56) References Cited

U.S. PATENT DOCUMENTS

| | | | | |
|---|---|---|---|---|
| 4,561,286 A | 12/1985 | Sekler et al. | ............... | 73/24.06 |
| 4,735,081 A | 4/1988 | Luoma et al. | ............... | 73/24.06 |
| 4,807,994 A * | 2/1989 | Felch et al. | ................... | 356/326 |
| 5,373,359 A | 12/1994 | Woollam et al. | ............... | 356/328 |
| 5,666,201 A | 9/1997 | Johs et al. | ................... | 356/369 |
| 5,706,212 A | 1/1998 | Thompson et al. | ......... | 364/525 |
| 5,872,632 A | 2/1999 | Moore | ......................... | 356/369 |
| 5,963,327 A | 10/1999 | He et al. | ...................... | 356/369 |
| 6,034,777 A | 3/2000 | Johs et al. | ................... | 356/369 |
| 6,125,687 A | 10/2000 | McClelland | ............... | 73/19.01 |
| 6,353,477 B1 | 3/2002 | Johs et al. | ................... | 356/369 |
| 6,456,376 B1 | 9/2002 | Liphardt et al. | ............. | 356/369 |
| 2004/0256961 A1* | 12/2004 | Namba et al. | ............... | 310/365 |
| 2004/0257567 A1* | 12/2004 | Woollam et al. | ............. | 356/369 |

OTHER PUBLICATIONS

"Surace Specific Kinetics of Lipid Vesicle Adsorbtion Measured With a Quartz Microbalance", Keller et al., Biophysical Journal, vol. 75, (1998).

"Simultaneous Monitoring of Protein Adsorbtion at the Solid-Liquid Interface From Sessile Solution Droplets by Ellipsometry and Axisymmetric Drop Shape Analysis by Profile", Noordmans et al., Colloids and Surfaces B: Biointerfaces 15, (1999).

"Characterization of PNA and DNA Immobilization and Subsequent Hybridization with DNA Using Acoustic Shear-Wave Attenuation Measurements", Hook et al., Langmuir 17, (2001).

(Continued)

*Primary Examiner*—Michael P. Stafira
(74) *Attorney, Agent, or Firm*—James D. Welch

(57) ABSTRACT

A combined ellipsometer and oscillator system and method of decorrelated determination of thickness and optical constants of deposited materials. In use the ellipsometer determines the product of thickness and optical constant, and the oscillator system changes frequency of oscillation proportional to the thickness of material deposited upon a surface of an element therein.

9 Claims, 2 Drawing Sheets

OTHER PUBLICATIONS

"Relaxation Dynamics in Ultrathin Polymer Films", Forrest et al., Physical Review E, vol. 58, No. 2, (1998).

"Structural Changes in Hemoglobin During Adsorbtion to Soild Surfaces: Effects of Ph, Ionic Strentth, and Ligand Binding", Hook et al., Proc. Natl. Acad. Sci., vol. 95, (1998).

"Regression Claibration Method for Rotating Element Ellipsometer", Johs, Thin Film Solids 234 (1993).

"Automatic Rotating Element Ellipsometers: Calibration, Operation and Real-time Applications", Rev. Sci. Instrum. 61 (8) (1990).

* cited by examiner

COMBINED USE OF OSCILLATING MEANS AND ELLIPSOMETRY TO DETERMINE UNCORRELATED EFFECTIVE THICKNESS AND OPTICAL CONSTANTS OF ACCUMULATED MATERIAL

This Application claims Benefit of Provisiona Application 60/437,024 Filed Dec. 31, 2002.

TECHNICAL AREA

The disclosed invention relates to systems and methods for simultaneously determining thickness and refractive indicies of materials, and more specifically to a combined ellipsometer and oscillating means system and method, wherein said oscillating means changes frequency of oscillation when material is deposited thereupon.

BACKGROUND

It is well known to use ellipsometry to determine thickness and optical constants of thin film materials. It is also known that ellipsometry provides a correlated product of thickness and refractive index. One known approach to breaking the correlation is to investigate two samples which have different thicknesses of the same material thereupon, and simultaneously perform regression of mathematical models for the two samples onto ellipsometric data obtained from each. The presently disclosed invention proposes a different approach to breaking the identified correlation involving gaining insight to the "effective thickness", (ie. thickness per se. as modified by surface coverage, roughness and/or porosity etc.) of a material caused to accumulate on the surface of an oscillating means, and using said insight in evaluating the product of the "effective" thickness and optical constants via ellipsometric techniques. That is, if an effective thickness of a material is determined by other techniques, and the product of said effective thickness and refractive index of a material is determined by ellipsometric techniques, then the refractive index can be determined by a simple division.

A Search for relevant reference material has provided a Patent:

U.S. Pat. No. 6,125,687 to McClelland et al. which describe a system for determining outgassing comprising a microbalance.

U.S. Pat. No. 4,561,286 to Sekler et al. which disclosed a piezoelectric detector.

U.S. Pat. No. 4,735,081 to Luoma et al. which discloses a detector for detecting vapors is gaseous fluids comprising a crystal oscillator.

Articles which were identified are:

"Surace Specific Kinetics of Lipid Vesicle Adsorbtion Measured With a Quartz Microbalance", Keller et al., Biophysical Journal, Vol. 75, (1998). This article discusses simultaneous frequency and dissipation measurments performed on QCM provide an efficient approach to measuring the kinetics of lipid vesicle adsorbtion and characterizing adsorbed layers.

"Simultaneous Monitoring of Protein Adsorbtion at the Solid-Liquid Interface From Sessile Solution Droplets by Ellipsometry and Axisymmetric Drop Shape Analysis by Profile", Noordmans et al., Colloids and Surfaces B: Biointerfaces 15, (1999). This article discusses combination of aqueous phase atomic force microscopy, ellipsometry and axisymmetric drop shape analysis by profile (ADSA-P).

"Characterization of PNA and DNA Immobilization and Subsequent Hybridization with DNA Using Acoustic Shear-Wave Attenuation Measurements", Hook et al., Langmuir 17, (2001). This article discusses combined use of a quartz microbalance and dissipation monitoring can characterize the bound state of single-stranded peptide nucleic acid (PNA) and deoxyribose nucleic acid (DNA).

"Relaxation Dynamics in Ultrathin Polymer Films", Forrest et al., Physical Review E, Vol. 58, No. 2, (1998). This paper describes combined application of Photon Correlation Spectroscopy and Quartz Balance Microbalance.

"Structural Changes in Hemoglobin During Adsorbtion to Solid Surfaces: Effects of Ph, Ionic Strentth, and Ligand Binding", Hook et al., Proc. Natl. Acad. Sci., Vol. 95, (1998). This aricle describes application of a Quartz Microbalance technique to follow Hb adsorption onto a surface. The Quartz Crystal Microbalance (QCM) system is described in this article as comprising a disk shaped, AT-cut Piezoelectric Quartz Crystal with metal electrodes deposited on two faces. In use the crystal is excited to oscillation in the thickness shear mode at its fundamental resonance frequency (f), by applying a RF Voltage across the electrodes near the resonant frequency. A small mass ($\Delta M$) added to the electrode induces a decrease in the resonant frequency ($\Delta f$) which is proportional to the ($\Delta m$), providing that the mass is evenly distributed, does not slip on the electrode and is sufficiently rigid and/or thin to have negligible internal friction. An equation is given which provides a quantitative descriptions:

$$\Delta M = (C \Delta f)/n$$

where $C(=17.7$ ng cm$^{-2}$ Hz$^{-1}$ at f=5 MHz), is the mass-sensitivity constant and $n(=1, 3, \ldots)$ is the overtone number.

Also disclosed are materials from "Q-SENSE" which disclose Quartz Micro-Balance systems:

"Q-SENSE D300";

"QCM-D Applications, Biosurfaces in Depth";

"Investigting the Sticking Power of Blue Mussels".

Finally, the methodology of ellipsometry is described in many references such as U.S. Pat. No. 5,373,359 to Woollam et al., U.S. Pat. No. 5,872,630 to Johs et al., U.S. Pat. No. 5,963,327 to He et al., U.S. Pat. No. 6,353,477 to Johs et al., U.S. Pat. No. 6,034,777 to Johs et al., U.S. Pat. No. 6,456,376 to Liphardt et al., U.S. Pat. No. 5,706,212 to Thompson et al. and U.S. Pat. No. 5,666,201 to Johs et al. An article by Johs titled "Regression Claibration Method for Rotating Element Ellipsometer", Thin Film Solids 234 (1993); an Article by Collins titled "Automatic Rotating Element Ellipsometers: Calibration, Operation and Real-time Applications", Rev. Sci. Instrum. 61 (8) (1990), and a book by Azzam & Bashara titled "Ellipsometry and Polarized Light", North-Holland (1977) is also disclosed.

Briefly, ellipsometry causes a polarized beam of electromagentic radiation to interact with a sample surface and then enter a detector. Changes in polarization state in the beam caused by the sample are represented by ellipsometric PSI and DELTA which are identified by:

$$\rho = rp/rs = \text{Tan}(\psi) \exp(i\Delta)$$

where $r_p$ and $r_s$ are orthogonal components of the beam perpendicular and parallel to, respectively, the sample surface. A mathematical model of the Sample is proposed and a regression procedure applied to convert the PSI and DELTA values to Sample representing values such as correlated thickness and optical constant values corresponding to various wavelengths and angles of incidence of the beam to the sample surface.

The forgoing references are incorporated by reference herein.

Even in view of known Prior Art, need remains for a system and method to combine Spectroscopic Ellipsometry and Quartz Microbalance techniques to the end of providing uncorrelated determination of both thickness and optical constants of deposited materials.

DISCLOSURE OF THE INVENTION

The disclosed invention comprises a method of determining an effective thickness of a material caused to accumulate on a surface, in uncorrelated combination with optical constants of said material caused to accumulate on said surface or another surface.

The disclosed invention comprises a method of determining an effective thickness of a material caused to accumulate on a surface, in uncorrelated combination with optical constants of said material caused to accumulate on said surface, comprising the steps of:

a) providing an oscillating means having a surface area, said oscillating means being a part of an oscillator circuit such that it is caused to physically vibrate or support resonant or non-resonant acoustic waves when electrical potential is applied thereto;

b) simultaneously or sequentially:
  b1) causing material to accumulate onto the surface of said oscillating means before and/or while it is caused to vibrate or support resonant or non-resonant acoustic waves at a frequency; and
  b2) causing a beam of electromagnetic radiation to interact with said surface area of said oscillating means and then enter a data detector;

c) in functional conjunction with step b) determining a relationship between a change in frequency of said oscillating means vs. effective thickness of material accumulated thereupon, and providing a mathematical model of the oscillating means and accumulated material system which includes said effective thickness, and optical constants of the accumulated material;

d) analyzing change in frequency of said oscillating means to determine effective thickness of said accumulated material, and performing regression of the data detector provided data onto said mathematical model to determine optical constants of said accumulated material in view of said determined effective thickness.

The "effective thickness" can be viewed as an actual thickness per se., modified where necessary by such as surface coverage, roughness and material porosity.

The source of the beam of electromagnetic radiation which caused to interact with material deposited on said surface, can be an ellipsometer or polarimeter system which comprises, in a polarization state generator, a source of electromagnetic radiation and polarizing means, and in which said data detector is part of a polarization state detector which further comprises analyzer means.

Data accumulation can involve monitoring the change of frequency of the oscillating means as material is caused to accumulate on a surface thereof, in functional combination with application of an ellipsometer or polarimeter system which comprises a source of electromagnetic radiation, polarizing means, analyzer means and a data detector to produce a polarized beam of electromagnetic radiation, cause it to interact with the material which has accumulated on the surface of the oscillating means, then pass through the analyzer and enter the data detector. It is noted that the oscillation frequency change data can be accumulated in real time during the accumulation of the said material on said surface of said oscillating means, or it can be taken before and after an accumulation, or at various stages during an accumulation. The polarimeter or ellipsometer data can also be taken in real time during material accumulation, or thereafter, or at various stages during an accumulation.

The described methodology can be useful in providing insight to material accumulated on, for instance, the surface of a vibrating quartz crystal which is part of an oscillator circuit.

Another disclosed invention method comprises determining an effective thickness of a material caused to accumulate on a surface in uncorrelated combination with optical constants of said material caused to accumulate on another surface comprising the steps of:

a) providing a sample having a surface area, and an oscillating means having a separate surface area, said oscillating means being a part of an oscillator circuit such that it is caused to physically vibrate or support resonant or non-resonant acoustic waves when electrical potential is applied thereto;

b) causing material to simultaneously acumulate on said surface of said sample and said surface of said oscillating means;

c) simultaneously causing:
  c1) material to accumulate onto the surface of said oscillating means before and/or while it is caused to vibrate or support resonant or non-resonant acoustic waves at a frequency; and
  c2) material to accumulate onto the surface of said sample before and/or while a beam of electromagnetic radiation to interact with said surface area of said sample and then enter a data detector;

said material accumulated on both surfaces being substantially similar;

d) in functional conjunction with step c) determining a relationship between a change in frequency of said oscillating means vs. effective thickness of material accumulated thereupon; and providing a mathematical model of the sample and accumulated material system which includes effective thickness and optical constants of the accumulated material;

e) analyzing change in frequency of said oscillating means to determine effective thickness of said accumulated material, and performing regression of the data detector provided data onto said mathematical model to determine optical constants of said accumulated material in view of said determined effective thickness.

The "effective thickness" can be viewed as an actual thickness per se., modified where necessary by such as surface coverage, roughness and material porosity.

The source of the beam of electromagnetic radiation which caused to interact with material deposited on said surface, can be an ellipsometer or polarimeter system which comprises, in a polarization state generator, a source of electromagnetic radiation and polarizing means, and in which said data detector is part of a polarization state detector which further comprises analyzer means.

Data accumulation can involve monitoring the change of frequency of the oscillating means as material is caused to accumulate on a surface thereof, in functional combination with application of an ellipsometer or polarimeter system which comprises a source of electromagnetic radiation, polarizing means, analyzer means and a data detector to produce a polarized beam of electromagnetic radiation, cause it to interact with the material which has accumulated on the surface of the oscillating means, then pass through the analyzer and enter the data detector. It is noted that the oscillation frequency change data can be accumulated in real time during the accumulation of the said material on said surface of said oscillating means, or it can be taken before and after an accumulation, or at various stages during an accumulation. The polarimeter or ellipsometer data can also be taken in real time during material accumulation, or thereafter, or at various stages during an accumulation.

It is specifically noted that said accumulated material can be deposited, (eg. evaporation of a metal), or grown, (eg. biological), or caused to accumulate by any functional technique.

It is also disclosed that where the refractive index of a material is known or can be determined independently, then ellipsometry can be applied to determine the product of said refractive index and thickness, and by division the thickness of the material can be obtained. A change in frequency of an oscillating means onto which some of said material is deposited, in combination with its surface area, can then be utilized to determine the material density.

The disclosed invention will be better understood by reference to the Detailed Description of this Specification in combination with the Drawings.

SUMMARY OF THE INVENTION

It is therefore an objective and/or purpose of the disclosed invention to teach a system comprising a Quartz Microbalance and an ellipsometer system.

It is another objective and/or purpose of the disclosed invention to teach a method for uncorrelated determination of thickness and optical constants of materials.

It is yet another objective and/or purpose of the disclosed invention to teach a method for determining density of a material where its optical constants are known or can be otherwise determined, where ellipsometry is applied to determine thickness of a material on an oscillating means surface of known geometry.

Other objectives and/or purposes of the disclosed invention will be apparent upon a reading of the Specification and claims.

DETAILED DESCRIPTION

Figure 1:
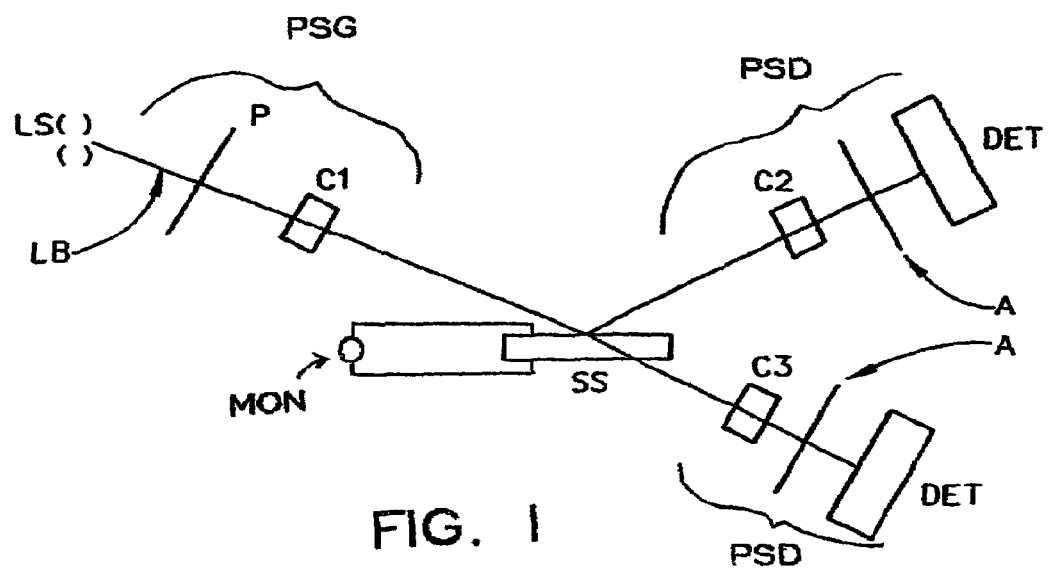
FIG. 1, there is demonstrated an Ellipsometry system.

Turning now to FIG. 1, there is demonstrated an Ellipsometry system. Note that a Source of Electromagentic Raditiaon (LS) provides a beam (LB) which has a polarization state set by Polarizer (P) and Optional Compensator (C1) prior to interaction with a Sample (SS). Shown after the Sample (SS) are both Reflection and Transmission scenarios, each of comprise an Analyzer (A) and Optional Compensator (C2) (C3). Note that indications of Polarization State Generator (PSG) and Polarization State Detector (PSD) are shown.

Figure 2:
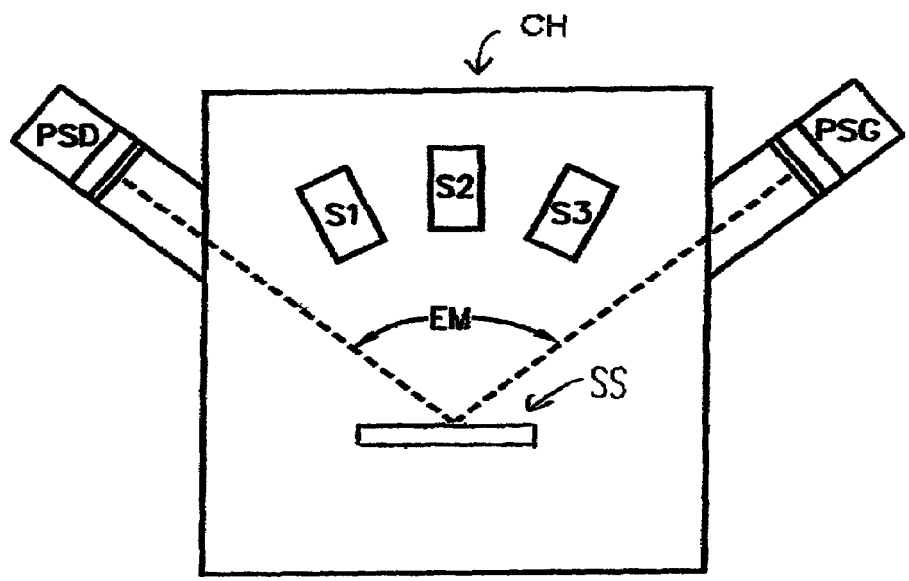
FIG. 2 demonstrates a system for depositing materials onto Samples (SS).

FIG. 2 demonstrates a system for depositing materials onto Samples (SS). Shown are a Chamber (C) to which are affixed Polarization State Generator (PSG) and Polarization State Detector (PSD), as well as Sources (S1) (S2) (S3) of Materials to Deposit onto the Sample (SS), or at least release into the vicinity thereof. It is noted that materials to be deopsited can be dielectrics, metals, insulators etc., or can comprise organic materials and the Sample (SS) can have a surface which has an affinity for accumulating materials released from a Source (S1) (S2) (S3) of Material. Typical application of ellipsometry in a FIG. 2 configuration provides data that identifies a product of thickness and refractive index of, for instance, a thin film deposited on the upper surface of the shown Sample (SS).

Figure 3:
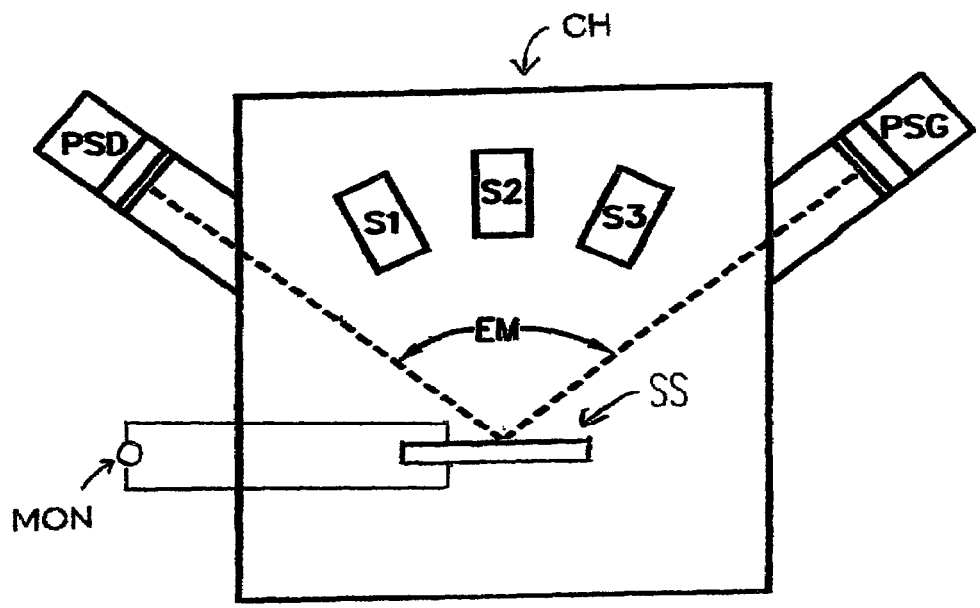
FIG. 3 shows that the Sample (SS) which is subjected to ellipsometric investigation, can have a Monitor (MON) electrically conntected thereto which includes excitation and resonant frequency detecting capability.
Figure 4:
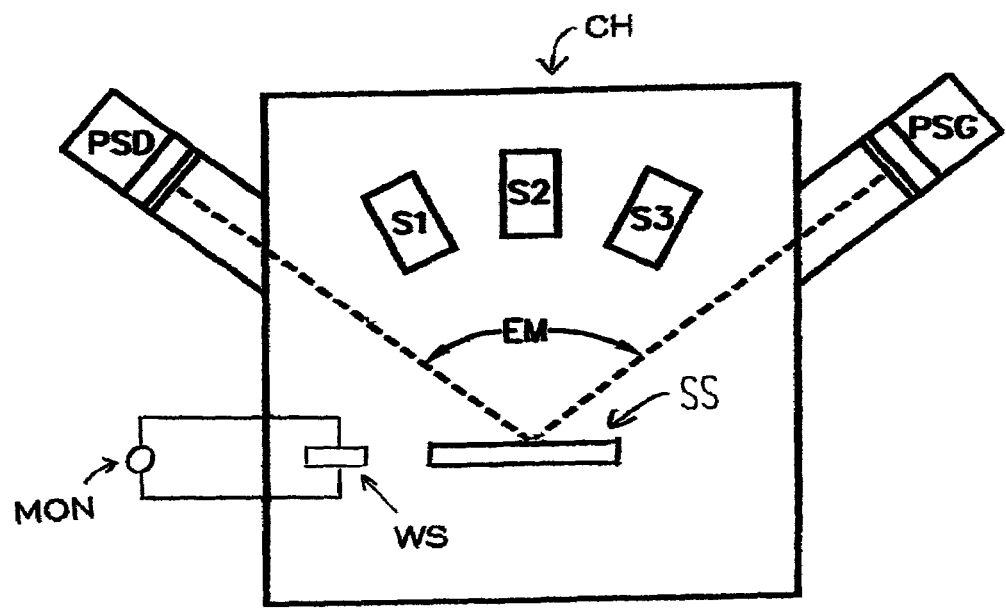
FIG. 4 demonstrates that the small mass can be added to a witness sample (WS) which is separately monitored for change in resonant frequency, thereby not requiring the Sample (SS) which is subjected to ellipsometric investigation to be changed by attachment of electrodes thereto.

FIG. 3 shows that the Sample (SS) which is subjected to ellipsometric investigation, can have a Monitor (MON) electrically conntected thereto which includes excitation and resonant frequency detecting capability. As disclosed in the Background Section, a small mass ($\Delta m$) added to the Sample (SS) induces a decrease in the resonant frequency ($\Delta f$) which is proportional to the ($\Delta m$). FIG. 4 demonstrates that the small mass can be added to a witness sample (WS) which is separately monitored for change in resonant frequency, thereby not requiring the Sample (SS) which is subjected to ellipsometric investigation to be changed by attachment of electrodes thereto. Similar separate system configurations are often utilized in Vacuum Deposition of materials onto Samples (SS), but not in conjunction with application of ellipsometry to enable de-correlation of deposited layer effective thickness and optical constants.

In general it is to be understood that the Chamber (CH) can be a vacuum chamber, a controlled ambient chamber or a chamber in which fluid is present and the Sources (S1) and/or (S2) and/or (S3) can provide any functional material which deposits onto the surface of a Sample (SS), and optionally onto another surface which is part of an ocillating circuit. In addition, as shown in FIG. 1, mateial can be caused to be present on a surface of a Sample (SS) outide of a chamber.

Finally, it is noted that the change in frequency of an oscillating means, as a function of deposited material, is directly proportional to the mass of the deposited material. Based on surface geometry, this correlates to density and thickness of the material. Further, elipsometric models can include parameters which correspond to surface coverage, roughness and material porosity. Depending on what is known and what is desired to be evaluated, the various methods of this invention are applied.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the claims.

We claim:

1. A method of determining an effective thickness of a material caused to accumulate on a surface, in uncorrelated combination with determination of optical constants of said material, comprising the steps of:
- a) providing an oscillating means having a surface area, said oscillating means being a part of an oscillator circuit such that it is caused to physically vibrate or support resonant or non-resonant acoustic waves when electrical potential is applied thereto;
- b) simultaneously or sequentially:
  - b1) causing material to accumulate onto the surface of said oscillating means before and/or while it is caused to vibrate and/or support resonant or non-resonant acoustic waves at a frequency; and
  - b2) causing a beam of electromagnetic radiation to interact with said surface area of said oscillating means and then enter a data detector;
- c) in functional conjunction with step b) determining a relationship between a change in frequency of said oscillating means vs. effective thickness material accumulated thereupon, and providing a mathematical model of the oscillating means and accumulated material system which includes said effective thickness, and optical constants of the accumulated material;
- d) analyzing change in frequency of said oscillating means to determine effective thickness of said accumulated material, and performing regression of the data detector provided data onto said mathematical model to determine optical constants of said accumulated material in view of said determined effective thickness.

2. A method of determining uncorrelated thickness and optical constants of a deposited material as in claim 1 in which the beam of electromagnetic radiation caused to interact with said surface area of said oscillating means, upon which material is deposited, and then enter a data detector is provided by an ellipsometer or polarimeter system which comprises, in a polarization state generator, a source of electromagnetic radiation and polarizing means and in which said data detector is part of a polarization state detector which further comprises analyzer means.

3. A method of determining uncorrelated thickness and optical constants of a deposited material as in claim 1 in which the oscillating means is a quartz crystal.

4. A method of determining uncorrelated thickness and optical constants of a deposited material as in claim 1 in which the thickness is characterized by at least one selection from the group consisting of:
- thickness per se;
- surface coverage;
- roughness; and
- porosity.

5. A method of determining uncorrelated thickness and optical constants of a deposited material comprising determining an effective thickness of a material in uncorrelated combination with optical constants of said material, comprising the steps of:
- a) providing a sample having a surface area, and an oscillating means having a separate surface area, said oscillating means being a part of an oscillator circuit such that it is caused to physically vibrate or support resonant or non-resonant acoustic waves when electrical potential is applied thereto;
- b) causing material to simultaneously acumulate on said surface of said sample and said surface of said oscillating means;
- c) simultaneously causing:
  - c1) material to accumulate onto the surface of said oscillating means before and/or while it is caused to vibrate or support resonant or non-resonant acoustic waves at a frequency; and
  - c2) material to accumulate onto the surface of said sample before and/or while a beam of electromagnetic radiation to interact with said surface area of said sample and then enter a data detector;

said material accumulated on both surfaces being substantially similar;
- d) in functional conjunction with step c) determining a relationship between a change in frequency of said oscillating means vs. effective thickness of material accumulated thereupon, and providing a mathematical model of the sample and accumulated material system which includes effective thickness and optical constants of the accumulated material;
- e) analyzing change in frequency of said oscillating means to determine effective thickness of said accumulated material, and performing regression of the data detector provided data onto said mathematical model to determine optical constants of said accumulated material in view of said determined effective thickness.

6. A method of determining uncorrelated thickness and optical constants of a deposited material as in claim 5 in which the beam of electromagnetic radiation caused to interact with said surface area of said oscillating means, upon which material is deposited, and then enter a data detector is provided by an ellipsometer or polarimeter system which comprises, in a polarization state generator, a source of electromagnetic radiation and polarizing means, and in which said data detector is part of a polarization state detector which comprises analyzer means.

7. A method of determining uncorrelated thickness and optical constants of a deposited material as in claim 5 in which the oscillating means is a quartz crystal.

8. A method of determining uncorrelated thickness and optical constants of a deposited material as in claim 5 in which the thickness is characterized by at least one selection from the group consisting of:
- thickness per se;
- surface coverage;
- roughness; and
- porosity.

9. A method of determining density of material deposited onto a surface of an oscillating means comprising the steps of:
- a) depositing material of known refractive index onto a surface of an oscillating means of known surface area, and detecting a change in the frequency of oscillation;
- b) by application of an ellipsometer or polarimeter determining the product of the refractive index and thickness of said deposited material;
- c) dividing the product of the refractive index and thickness of said deposited material determined in step b, by the known refractive index of said material to determine an effective thickness;
- d) utilizing the known surface area of the oscillating means onto which said material is deposited, and the thickness of said material determined in step c, and the change in frequency of the oscillating means detected in step a which is proportional to the mass of the deposited material, determining the mass per unit volume.

* * * * *